United States Patent [19]

Haber et al.

[11] Patent Number: 5,756,804
[45] Date of Patent: May 26, 1998

[54] HOMOGENEOUS PROCESS FOR CARRYING OUT CROSS-COUPLING REACTIONS

[75] Inventors: Steffen Haber, Germersheim/Rhein; Hans-Jerg Kleiner, Kronberg, both of Germany

[73] Assignee: Hoechst Aktiengesellschaft, Frankfurt, Germany

[21] Appl. No.: 686,167

[22] Filed: Jul. 24, 1996

[30] Foreign Application Priority Data

| Jul. 25, 1995 | [DE] | Germany | 195 27 118.1 |
| Sep. 25, 1995 | [DE] | Germany | 195 35 528.8 |
| May 17, 1996 | [DE] | Germany | 196 20 023.7 |

[51] Int. Cl.[6] .......................... C07C 255/50; C07C 2/00; C07C 253/30
[52] U.S. Cl. .......................... 558/411; 548/235; 548/252; 549/369; 549/430; 562/493; 564/80; 564/161; 568/592
[58] Field of Search .................. 548/235, 252; 549/369, 430; 558/411; 562/493; 564/80, 161; 568/592

[56] References Cited

U.S. PATENT DOCUMENTS

| 5,057,618 | 10/1991 | Herrmann et al. | 556/21 |
| 5,550,236 | 8/1996 | Schlosser et al. | 544/238 |

FOREIGN PATENT DOCUMENTS

| 0571770 | 12/1993 | European Pat. Off. . |
| 43 40 490 | 6/1994 | Germany . |
| A 44 26 671 | 2/1996 | Germany . |
| WO 94/10105 | 5/1994 | WIPO . |

OTHER PUBLICATIONS

J. Org. Chem. 1994, 59, pp. 6095–6097 entitled "Fluoride-Mediated Boronic Acid Coupling Reactions" by Wright et al.

J. Med. Chem. 1991, 34, pp. 2919–2922 entitled "Potent, Orally Active Imidazo [4,5-b]pyridine–Based Angiotensin II Receptor Antagonists", by Mantlo et. al.

*Primary Examiner*—Bernard Dentz
*Attorney, Agent, or Firm*—Scott E. Hanf

[57] ABSTRACT

A process for preparing polycyclic aromatic compounds, which comprises reacting a) an aromatic boron compound with b) an aromatic halogen compound or an aromatic perfluoroalkylsulfonate in the presence of c) a base, d) a nickel or palladium catalyst, e) a phosphorus-containing ligand and f) a polyhydric alcohol, a sulfoxide or sulfone.

The process gives high yields, in particular also in the coupling of chloroaromatics.

9 Claims, No Drawings

HOMOGENEOUS PROCESS FOR CARRYING OUT CROSS-COUPLING REACTIONS

The invention relates to a process for preparing polycyclic aromatic compounds by a cross-coupling reaction of aromatic boron compounds and aromatic halogen compounds or perfluoroalkylsulfonates using nickel or palladium catalysis.

Cross-coupling reactions of aromatic boron compounds such as boronic acids and aromatic halogen compounds or perfluoroalkylsulfonates have for some years been used to an increasing extent for building up polycyclic aromatic systems. For example, such processes are used for producing pharmaceutical active compounds and components of liquid crystal mixtures.

However, the catalysts usually used, for example Pd[P(Ph$_3$)]$_4$ or PdCl$_2$(4PPh$_3$)4NaBH$_4$, give the coupling products in appreciable yields only when bromoaromatics or iodoaromatics are used. The high costs of these starting compounds make economical transfer of the process to a larger production scale difficult.

If recourse is to be made to the lower-cost chloroaromatics as starting compounds, it is necessary, as described in DE-A-43 40 490, to use a palladium catalyst and lipophilic, aliphatic phosphine ligands.

However, such phosphines are not only complicated to prepare and very oxidation sensitive, but they cannot be reused. Furthermore, if the phosphine ligand does not also contain cycloalkyl groups, the yields of the process described in DE-A 43 40 490 are very much in need of improvement.

It was therefore desirable to develop a process which makes possible the coupling of aromatic chlorine compounds with aromatic boron compounds in high yields, without the need to use lipophilic, aliphatic phosphines containing cycloalkyl groups.

It has now surprisingly been found that chlorine-substituted and other halogen-substituted or perfluoroalkylsulfonate-substituted aromatics and aromatic boron compounds can be coupled in high yields in the presence of a phosphorus-containing complexing ligand using palladium or nickel catalysis if one or more polyhydric alcohols, sulfoxides or sulfones are added.

The invention accordingly provides a process for preparing polycyclic aromatic compounds, which comprises reacting a) an aromatic boron compound with b) an aromatic halogen compound or an aromatic perfluoroalkylsulfonate in the presence of c) a base, d) a nickel or palladium catalyst, e) a phosphorus-containing ligand and f) a polyhydric alcohol, a sulfoxide or sulfone.

The process of the invention enables polycyclic aromatic compounds to be prepared economically in very good yields and at the same time very high purity, in particular without contamination by phosphine ligands. It is also well suited to the coupling of chloroaromatics and therefore offers considerable economic advantages.

The process is chemoselective, so that even electrophilic groups such as esters and nitrites do not impair the course of the reaction.

Preferred polyhydric alcohols are those which are water-soluble. Particular preference is given to glycols, glycerol, oligoglycerides which can also be partially esterified, diethylene, triethylene and tetraethylene glycols or polyethylene glycols of the formula (I),

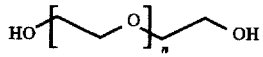

polyhydric alkanols or alkenols such as 1,4-butanediol, 1,3-propanediol, 1,2-propanediol, pentaerythritol, 2-ethylhexane-1,3-diol, 2-hydroxymethyl-2-methylpropane-1,3-diol, 2-methylpentane-2,4-diol, cis-1,4-butenediol, polyhydric cycloalkanols such as cyclohexanediol, polyhydric aryl-containing alkanols such as 1-phenylethane-1,2-diol, polyhydric aminoalcohols such as diethanolamine, triethanolamine, 2-amino-2-methylpropane-1,3-diol, 3-(aminomethyl)propane-1,2-diol, 3-aminopropane-1,2-diol, 2-aminopropane-1,3-diol oxalate, 3-(diethylamino)propane-1,2-diol, ethylenediamine-N,N,N',N'-tetra-2-propanediol, polyhydric iminoalcohols such as N-butyl- and N-tert-butyl-2,2'-iminodiethanol, 1,1'-iminodi-3-propanol, N-methyl-2,2'-iminodiethanol, N-phenyl-2,2'-iminodiethanol, or compounds such as 1,1',1"-nitrilotri-2-propanol, 1,3,5-tri(2-hydroxyethyl)isocyanuric acid and dihydroxyacetone.

Very particular preference is given to glycol, glycerol, 1,4-butanediol, 1,2-propanediol, triethylene glycol, diethylene glycol, diethanolamine and triethanolamine and of these glycol, glycerol, 1,4-butanediol and 1,2-propanediol in particular.

It is naturally also possible to use a plurality of polyhydric alcohols.

Preferred sulfoxides or sulfones are those of the formula (II):

n = 0, sulfoxide
n = 1, sulfon

R$^1$, R$^2$ are aliphatic or aromatic hydrocarbons which may be substituted or linked to one another.

Particularly preferred sulfoxides are dimethyl sulfoxide (DMSO), diphenyl sulfoxide, methyl phenyl sulfoxide and dibenzyl sulfoxide.

Particularly preferred sulfones are bis(4-hydroxyphenyl) sulfone, bis(4-aminophenyl) sulfone (Dapson), bis(3-aminophenyl) sulfone, dimethyl sulfone, diphenyl sulfone, sulfolane, 3-sulfolene.

Preference is given to using water-soluble sulfoxides or sulfones. Particularly preferred water-soluble sulfoxides or sulfones are DMSO and sulfolane.

It is naturally also possible to use a plurality of sulfoxides or sulfones or mixtures thereof, if desired also with polyhydric alcohols.

Sulfonamides and aliphatic or aromatic sulfonates are also suitable for the process.

If the polyhydric, water-soluble alcohol or the sulfoxide or sulfolane do not serve as the only solvent, they are preferably added in a weight ratio of from 0.1 to 10 000, based on the catalyst.

Suitable phosphorus-containing ligands are preferably tri-n-alkylphosphines, triarylphosphines, dialkylarylphosphines, alkyldiarylphosphines and heteroarylphosphines such as tripyridylphosphine and trifurylphosphine, where the three substituents on the phosphorus can be identical or different, chiral or achiral and where one or more of the substituents can link the phosphorus groups of a plurality of phosphines and where part of this linkage can also be one or more metal atoms, phosphites, phosphinous esters and phosphonous esters, phosphors, dibenzophosphols and phosphorus-containing cyclic, oligocyclic or polycyclic compounds.

Particular preference is given to phosphines containing at least one aryl group on the phosphorus, i.e. triarylphosphines, diarylalkylphosphines and dialkylarylphosphines, and phosphites.

In systems containing an aqueous phase, particular preference is given to water-soluble phosphine ligands containing at least one aryl group.

Very particular preference is given to triarylphosphines. Most preferred are:

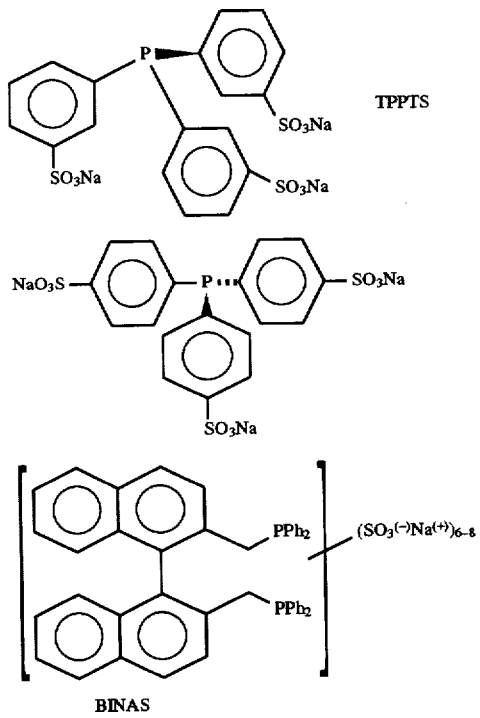

It is naturally also possible to use a plurality of phosphorus-containing ligands.

The phosphorus-containing ligands used according to the invention are known per se. Some of them are commercial products or they are described together with their synthesis in, for example, Houben-Weyl, Methoden der Organischen Chemie, Georg-Thieme-Verlag, Stuttgart.

Water-soluble ligands can be prepared, for example, by the method of W. A. Herrmann and C. W. Kohipainter, Angew. Chem. Int. Ed. Engl. 1993, 32, 1524 or the literature cited therein. The preparation of BINAS is described in EP-A 0 571 819 or U.S. Pat. No. 5,347,045.

The phosphorus-containing ligand is used in the process of the invention in an amount of from 0.001 to 20 mol %, preferably from 0.01 to 10 mol %, particularly preferably from 0.05 to 6 mol %, very particularly preferably from 0.1 to 6 mol %, based on the aromatic halogen compound or the aromatic perfluoroalkylsulfonate.

Catalysts used are palladium metal, palladium compounds or nickel compounds. The catalyst can also be applied to a solid support such as activated carbon or aluminum oxide.

Preference is given to palladium catalysts in which the palladium is present in the oxidation state (0) or (II), for example palladium ketonates, palladium acetylacetonates, nitrilepalladium halides, palladium halides, allylpalladium halides and palladium biscarboxylates, particularly preferably palladium ketonates, palladium acetylacetonates, palladium(II) halides, η-$^3$-allylpalladium halide dimers and palladium biscarboxylates. Very particular preference is given to palladium bisacetylacetonate, bis(benzonitrile) palladium dichloride, $PdCl_2$, $Na_2PdCl_4$, $Na_2Pd_2Cl_6$, bis(acetonitrile)palladium dichloride, palladium(II) acetate, palladium(II) propionate and palladium(II) butanoate.

The palladium compound can also be generated in situ, for example palladium(II) acetate by addition of palladium (II) chloride and sodium acetate.

The catalyst can already contain the phosphorus-containing ligand used according to the invention, but the ligand can also be added separately to the reaction mixture.

To carry out the process of the invention, preference is given to dissolving palladium or a palladium compound in a polyhydric alcohol, sulfoxide or sulfolane, preferably DMSO or glycol, admixing the solution with the phosphorus-containing ligand or a solution thereof and adding the catalyst solution thus formed to the remaining reactants.

Likewise preferred is dissolving palladium or a palladium compound in a polyhydric alcohol, sulfoxide or sulfolane, preferably DMSO or glycol, admixing this solution with the remaining reactants and subsequently adding the phosphorus-containing ligand or a solution thereof.

Particularly suitable starting compounds for preparing the catalyst according to these two methods are $Pd(II)Cl_2 3$ NaOAc, $Pd(ac)_2$, $K_2PdCl_4$, $Na_2PdCl_4$, $K_2PdCl_6$ and $Na_2PdCl_6$.

In the process of the invention, the catalyst is used in an amount of from 0.001 to 10 mol %, preferably from 0.01 to 5 mol %, particularly preferably from 0.05 to 3 mol %, very particularly preferably from 0.05 to 1.5 mol %, based on the aromatic halogen compound or the aromatic perfluoroalkylsulfonate.

Bases which are usually used in the process of the invention are alkali metal fluorides, alkali metal and alkaline earth metal hydroxides, alkali metal and alkaline earth metal carbonates, alkali metal hydrogen carbonates, alkali metal and alkaline earth metal acetates, alkali metal and alkaline earth metal alkoxides, and also primary, secondary and tertiary amines.

Particular preference is given to alkali metal fluorides, alkali metal and alkaline earth metal hydroxides, alkali metal and alkaline earth metal carbonates and alkali metal hydrogen carbonates. Very particular preference is given to alkali metal fluorides such as potassium fluoride and cesium fluoride, alkali metal hydroxides, such as sodium hydroxide and potassium hydroxide, and also alkali metal carbonates and alkali metal hydrogen carbonates such as lithium carbonate, sodium carbonate and potassium carbonate.

It is naturally also possible to add a plurality of bases.

In the process of the invention, the base is preferably added in an amount of from 100 to 1000 mol %, particularly preferably from 100 to 500 mol %, very particularly preferably from 100 to 400 mol %, most preferably from 100 to 290 mol %, based on the aromatic boron compound.

Preferred starting compounds for the process of the invention are, on the one hand, aromatic boron compounds of the formula (III), $$Aryl-BQ_1Q_2 \qquad (III)$$

where

Aryl is an aromatic radical and $Q_1$, $Q_2$ are identical or different and are —OH, $C_1$–$C_4$-alkoxy, $C_1$–$C_4$-alkyl, phenyl which may be unsubstituted or substituted by $C_1$–$C_4$-alkyl, $C_1$–$C_4$-alkoxy or halogen, or halogen or $Q_1$ and $Q_2$ together form a $C_1$–$C_4$-alkylenedioxy group, a methylene group which may be unsubstituted or substituted by one or two $C_1$–$C_4$-alkyl groups, or $Q_1$ and $Q_2$ and the boron atom are together part of a boroxane ring of the formula (IV):

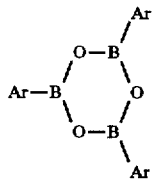
(IV)

Aryl is preferably a phenyl, naphthyl, pyrimidyl, pyridine, pyrazine, pyradazine, 1,3-thiazole, 1,3,4-thiadiazol or thiophenyl radical which can each be unsubstituted or substituted, for example by halogen, cyano, alkyl or alkoxy groups.

$Q_1$, $Q_2$ are preferably identical or different and are—OH, $C_1$–$C_4$-alkoxy or halogen or $Q_1$ and $Q_2$ together form a $C_1$–$C_4$-alkylenedioxy group or $Q_1$ and $Q_2$ and the boron atom are together part of a boroxane ring of the formula (IV):

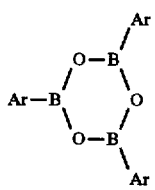
(IV)

Aryl is particularly preferably an unsubstituted or substituted phenyl or naphthyl group.

Very particularly preferred aromatic boron compounds are

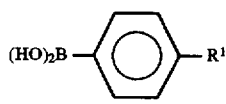

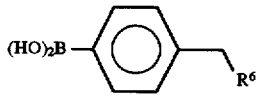

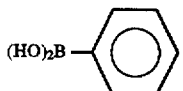

Very particularly preferred compounds are:

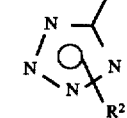

-continued

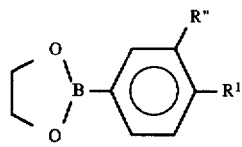

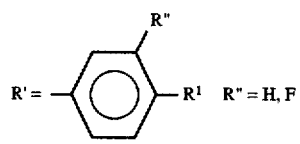
R" = H, F

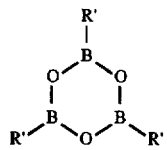

where $R^1$ and $R^2$ are benzyloxy, H, methyl, ethyl, propyl, butyl, pentyl, hexyl, heptyl, octyl, nonyl, decyl, undecyl, dodecyl, tridecyl, tetradecyl and pentadecyl, and also methoxy, ethoxy, propoxy, butoxy, pentoxy, hexoxy, heptoxy, octoxy, nonoxy, decoxy, undecoxy, dodecoxy, tridecoxy, tetradecoxy, pentadecoxy, CPh$_3$ and SiMe$_2$tBu, and $R^6$ is imidazole, quinoline, isoquinoline, dihydropyridine or pyrazole which can each be unsubstituted or substituted. Most preferred is p-tolueneboronic acid.

The aromatic boron compounds used are either known or can be prepared by methods known per se, as described in, for example, Houben Weyl, Methoden der Organischen Chemie, Georg Thieme-Verlag, Stuttgart, Volume 13/3a. Thus, it is possible, for example, to obtain boronic acids from aromatic alkali metal and magnesium compounds by reaction with trialkoxyboranes and subsequent hydrolysis.

The second class of starting compounds for the process of the invention are aromatic compounds of the formula (V)

Aryl—X (V)

where

Aryl is an aromatic radical and

X is Cl, Br, I or a perfluoroalkylsulfonate.

X is preferably Cl.

Aryl is preferably an unsubstituted or substituted phenyl, naphthyl, pyridine, pyrimidine, pyrazine, pyridazine, 1,3-thiazole, 1,3,4-thiadiazole or thiophene radical, where the substituent(s) are, for example, halogen, CN, alkyl, alkoxy or further aryl groups.

Particularly preferred compounds of the formula (V) are

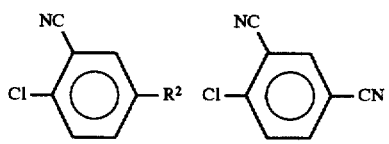

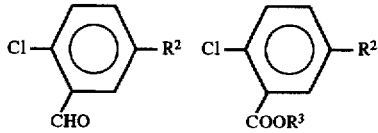

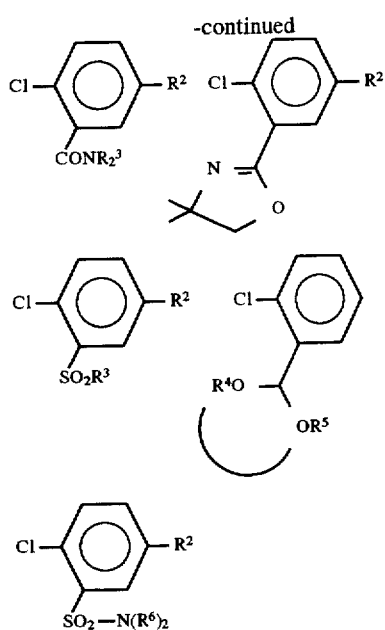

where $R^2$ and $R^3$ are benzyloxy, H, methyl, ethyl, propyl, butyl, pentyl, hexyl, heptyl, octyl, nonyl, decyl, undecyl, dodecyl, tridecyl, tetradecyl and pentadecyl, and also methoxy, ethoxy, propoxy, butoxy, pentoxy, hexoxy, heptoxy, octoxy, nonoxy, decoxy, undecoxy, dodecoxy, tridecoxy, tetradecoxy, pentadecoxy, $CPh_3$ and $SiMe_2Bu$; $R^4$, $R^5$ are methyl, ethyl, propyl, butyl, pentyl, hexyl, heptyl, octyl, nonyl, decyl, undecyl, dodecyl, tridecyl, tetradecyl, pentadecyl or $R^4$ and $R^5$ are together —$(CH_2)_2$— or $CH_2$)$_3$—.

Very particular preference is given to 2-chlorobenzonitrile.

The aromatic halogen compounds and perfluoroalkylsulfonates which are used are either known or can be prepared by known methods as described in, for example, Houben Weyl, Methoden der Organischen Chemie, Georg Thieme Verlag, Stuttgart, Volumes 5/3 and 5/4. For example, aromatic halides can be obtained by replacing the diazonium group of a corresponding diazonium salt by chlorine, bromine or iodine.

Furthermore, hydroxy-substituted nitrogen heterocycles can be converted into the corresponding halides by means of phosphorus trihalides and phosphoroxy trihalides.

To carry out the process of the invention, the starting materials, the base, palladium, the palladium compound or the nickel compound and the phosphorus-containing ligand are mixed according to the variants indicated above and reacted at a temperature of from 0 °to 200° C., preferably from 30° to 170° C., particularly preferably from 50° to 150° C., over a period of from 1 to 100 hours, preferably from 5 to 70 hours, particularly preferably from 5 to 50 hours.

The work-up is carried out by known methods with which those skilled in the art are familiar. For example, the product can be separated from the reaction mixture by extraction or precipitation and subsequently be further purified by methods matched to the respective product, for example recrystallization, distillation, sublimation, zone melting, melt crystallization or chromatography.

If the starting compounds are doubly functionalized aromatic boron compounds such as bisboronic acids and aromatic halogen compounds or perfluoroalkylsulfonates, the process of the invention is also suitable for preparing polymers which are used, for example, as organic electroluminescence materials.

The products of the process of the invention are polycyclic aromatic compounds, preferably ones derived from the formulae (II) and (IV). Examples of preferred products are

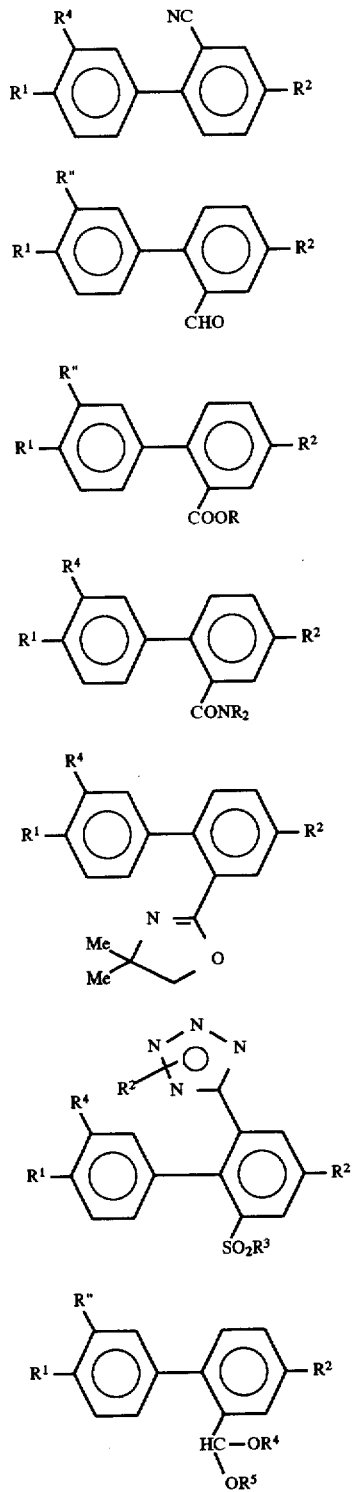

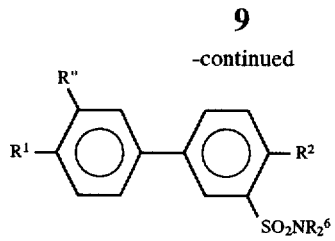

where

R¹, R² and R³ are benzyloxy, H, methyl, ethyl, propyl, butyl, pentyl, hexyl, heptyl, octyl, nonyl, decyl, undecyl, dodecyl, tridecyl, tetradecyl and pentadecyl, and also methoxy, ethoxy, propoxy, butoxy, pentoxy, hexoxy, heptoxy, octoxy, nonoxy, decoxy, undecoxy, dodecoxy, tridecoxy, tetradecoxy, pentadecoxy, $CPh_3$ and $SiMe_2{}^tBu$; R⁴, R⁵ are methyl, ethyl, propyl, butyl, pentyl, hexyl, heptyl, octyl, nonyl, decyl, undecyl, dodecyl, tridecyl, tetradecyl, pentadecyl or R⁴ and R⁵ are together —$(CH_2)_2$— or —$(CH_2)_3$— and R⁴ is H or F.

A particularly preferred product is 2-cyano4'-methylbiphenyl.

The compounds prepared according to the invention are suitable for use as liquid-crystalline materials or can be used as intermediates for, the preparation of further liquid-crystalline compounds. In addition, they are used as precursors for pharmaceuticals, cosmetics, fungicides, herbicides, insecticides, dyes, detergents and polymers, including additives for these.

Compounds prepared according to the invention, as are represented, for example, by the above formulae, are, in particular, valuable precursors for angiotensin II inhibitors (see, for example, Drugs of the Future 18 (1993) 428–432).

The present invention will now be illustrated by the examples described below, without being limited thereby.

EXAMPLES

A. Catalyst preparation:

C.1

0.388 g of palladium(II) chloride and 0.54 g of sodium acetate are dissolved in 24 ml of DMSO. The mixture is stirred for 30 minutes at room temperature. It is subsequently admixed with 14.6 ml of TPPTS/$H_2O$ solution (0.6 mol/l) and is stirred for a further 30 minutes.

C.2

0.388 g of palladium(II) chloride and 0.54 g of sodium acetate are dissolved in 24 ml of ethylene glycol. The mixture is stirred for a further 30 minutes at room temperature. It is subsequently admixed with 14.6 ml of TPPTS/$H_2O$ solution (0.6 mol/l) and stirred for a further 30 minutes.

C.3

0.388 g of palladium(II) chloride and 14.6 ml of TPPTS/$H_2O$ solution (0.6 mol/l) are stirred for 60 minutes at room temperature. This gives a yellow reaction solution of

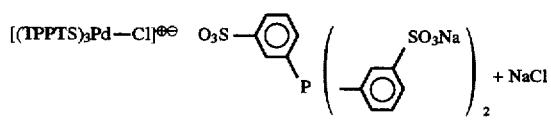

C.3.1

1.069 g tetrachloropalladic acid (20% by weight Pd in $H_2O$) are diluted with 24 ml $H_2O$, subsequently admixed with 14.6 ml of TPPTS/$H_2O$ solution (0.6 mol/l) and stirred for a further 30 minutes.

C.4

0.388 g of palladium(II) chloride and 0.33 g of potassium chloride are dissolved in 10 ml of water. This solution is admixed with 14.6 ml of TPPTS/$H_2O$ solution (0.6 mol/l).

B. Coupling reactions

Example 1

15 g of 2-chlorobenzonitrile, 14.8 g of p-tolueneboronic acid and 28.9 g of sodium carbonate were heated to 120° C. in 40 ml of glycol and 10 ml of water. At 80° C., 0.1 mol % of a catalyst solution prepared as described in C.1 was added. After the reaction was complete, 50 ml of xylene were added and the organic phase was separated off. Distillation gave 19 g of 2-cyano-4'-methylbiphenyl (mp. 140° C./mbar).

Example 2

15 g of 2-chlorobenzonitrile, 14.8 g of p-tolueneboronic acid and 28.9 g of sodium carbonate were heated to 120° C. in 40 ml of glycol and 10 ml of water. At 80° C., 0.1 mol % of a catalyst solution prepared as described in C.2 was added. After the reaction was complete, 50 ml of xylene were added and the organic phase was separated off. Distillation gave 18.5 g of 2-cyano-4'-methylbiphenyl (mp. 140° C./mbar).

Example 3

15 g of 2-chlorobenzonitrile, 14.8 g of p-tolueneboronic acid and 28.9 g of sodium carbonate were heated to 120° C. in 40 ml of glycol and 10 ml of water. At 80° C., 0.1 mol % of a catalyst solution prepared as described in C.3 was added. After the reaction was complete, 50 ml of xylene were added and the organic phase was separated off. Distillation gave 18.7 g of 2-cyano-4'-methylbiphenyl (mp. 140° C./mbar).

Example 4

15 g of 2-chlorobenzonitrile, 14.8 g of p-tolueneboronic acid and 28.9 g of sodium carbonate were heated to 120° C. in 40 ml of glycol and 10 ml of water. At 80° C., 0.1 mol % of a catalyst solution prepared as described in C.4 was added. After the reaction was complete, 50 ml of xylene were added and the organic phase was separated off. Distillation gave 18.1 g of 2-cyano-4'-methylbiphenyl (mp. 140° C./mbar).

Example 5

15 g of 2-chlorobenzonitrile, 14.8 g of p-tolueneboronic acid and 28.9 g of sodium carbonate were heated to 120° C. in 40 ml of glycol and 10 ml of water. At 80° C., 0.1 mol % of a catalyst solution prepared as described in C.3.1 was added. After the reaction was complete, 50 ml of xylene were added and the organic phase was separated off. Distillation gave 19 g of 2-cyano-4'-methylbiphenyl (mp. 140° C./mbar).

Example 6

15 g of 2-chlorobenzonitrile, 14.8 g of p-tolueneboronic acid and 12 g of sodium carbonate were heated to 120° C. in 40 ml of glycol and 10 ml of water. At 80° C., 0.1 mol % of a catalyst solution prepared as described in C. 1 was added. After the reaction was complete, 50 ml of xylene were added and the organic phase was separated off. Distillation gave 18.5 g of 2-cyano-4'-methylbiphenyl (mp. 140° C./mbar).

Example 7

15 g of 2-chlorobenzonitrile, 14.8 g of p-tolueneboronic acid and 12 g of sodium carbonate were heated to 120° C.

in 40 ml of glycol and 10 ml of water. At 80° C., 0.1 mol % of a catalyst solution prepared as described in C.3.1 was added. After the reaction was complete, 50 ml of xylene were added and the organic phase was separated off. Distillation gave 18.7 g of 2-cyano-4'-methylbiphenyl (mp. 140° C./mbar).

Example 8

15 g of 2-chlorobenzonitrile, 14.8 g of p-tolueneboronic acid and 12 g of sodium carbonate were heated to 120° C. in 40 ml of glycol and 10 ml of water. At 80° C., 0.1 mol % of a catalyst solution prepared as described in C.2 was added. After the reaction was complete, 50 ml of xylene were added and the organic phase was separated off. Distillation gave 18.1 g of 2-cyano-4'-methylbiphenyl (mp. 140° C./mbar).

Example 9

15 g of 2-chlorobenzonitrile, 14.8 g of p-tolueneboronic acid and 28.9 g of sodium carbonate were heated to 120° C. with 50 ml of p-xylene, 40 ml of glycol and 10 ml of water. At 80° C., a mixture of 24.7 mg of palladium acetate and 0.55 ml of TPPTS/$H_2O$ solution (0.6 molar) in 2.5 ml of DMSO was added.

After the reaction was complete, the phases were separated. The aqueous phase was washed with 50 ml of toluene. The combined organic phases were washed with 20 ml of water and subsequently dried over sodium sulfate. Crystallization from n-heptane gave 18.9 g of 2-cyano-4'-methylbiphenyl.

Example 10

15 g of 2-chlorobenzonitrile, 14.8 9 of p-tolueneboronic acid and 28.9 g of sodium carbonate were heated to 120° C. with 50 ml of p-xylene, 40 ml of glycerol and 10 ml of water. At 80° C., a mixture of 24.7 mg of palladium acetate and 0.55 ml of TPPTS/$H_2O$ solution (0.6 molar) in 2.5 ml of DMSO was added.

After the reaction was complete, the phases were separated. The aqueous phase was washed with 50 ml of toluene. The combined organic phases were washed with 20 ml of water and subsequently dried over sodium sulfate. Crystallization from n-heptane gave 18.5 g of 2-cyano-4'-methylbiphenyl.

Example 11

15 g of 2-chlorobenzonitrile, 14.8 9 of p-tolueneboronic acid and 28.9 g of sodium carbonate were heated to 120° C. with 50 ml of p-xylene, 40 ml of triethylene glycol and 10 ml of water. At 80° C., a mixture of 24.7 mg of palladium acetate and 0.55 ml TPPTS/$H_2O$ solution (0.6 molar) in 2.5 ml of DMSO was added.

After the reaction was complete, the phases were separated. The aqueous phase was washed with 50 ml of toluene. The combined organic phases were washed with 20 ml of water and subsequently dried over sodium sulfate. Crystallization from n-heptane gave 17.4 g of 2-cyano-4'-methylbiphenyl.

Example 12

15 g of 2-chlorobenzonitrile, 14.8 g of p-tolueneboronic acid and 28.9 g of sodium carbonate were heated to 120° C. with 50 ml of p-xylene, 40 ml of diethylene glycol and 10 ml of water. At 80° C., a mixture of 24.7 mg of palladium acetate and 0.55 ml of TPPTS/$H_2O$ solution (0.6 molar) in 2.5 ml of DMSO was added.

After the reaction was complete, the phases were separated. The aqueous phase was washed with 50 ml of toluene. The combined organic phases were washed with 20 ml of water and subsequently dried over sodium sulfate. Crystallization from n-heptane gave 18.2 g of 2-cyano-4'-methylbiphenyl.

Example 13

15 g of 2-chlorobenzonitrile, 14.8 g of p-tolueneboronic acid and 28.9 g of sodium carbonate were heated to 120° C. with 50 ml of p-xylene, 40 ml of diethanolamine and 10 ml of water. At 80° C., a mixture of 24.7 mg of palladium acetate and 0.55 ml of TPPTS/$H_2O$ solution (0.6 molar) in 2.5 ml of DMSO was added.

After the reaction was complete, the phases were separated. The aqueous phase was washed with 50 ml of toluene. The combined organic phases were washed with 20 ml of water and subsequently dried over sodium sulfate. Crystallization from n-heptane gave 17.5 g of 2-cyano-4'-methylbiphenyl.

Example 14

15 g of 2-chlorobenzonitrile, 14.8 g of p-tolueneboronic acid and 28.9 g of sodium carbonate were heated to 120° C. with 50 ml of p-xylene, 40 ml of triethanolamine and 10 ml of water. At 80° C., a mixture of 24.7 mg of palladium acetate and 0.55 ml of TPPTS/$H_2O$ solution (0.6 molar) in 2.5 ml of DMSO was added.

After the reaction was complete, the phases were separated. The aqueous phase was washed with 50 ml of toluene. The combined organic phases were washed with 20 ml of water and subsequently dried over sodium sulfate. Crystallization from n-heptane gave 17.8 g of 2-cyano-4'-methylbiphenyl.

Example 15

15 g of 2-chlorobenzonitrile, 15.8 g of p-tolueneboronic acid and 15.8 g of potassium fluoride were heated to 120° C. with 50 ml of p-xylene, 40 ml of glycerol and 10 ml of water. At 80° C., a mixture of 24.7 mg of palladium acetate and 0.55 ml of TPPTS/$H_2O$ solution (0.6 molar) in 2.5 ml of DMSO was added.

After the reaction was complete, the phases were separated. The aqueous phase was washed with 50 ml of toluene. The combined organic phases were washed with 20 ml of water and subsequently dried over sodium sulfate. Crystallization from n-heptane gave 18.2 g of 2-cyano-4'-methylbiphenyl.

Example 16

15 g of 2-chlorobenzonitrile, 15.8 g of p-tolueneboronic acid and 15.8 g of potassium fluoride were heated to 120° C. with 50 ml of p-xylene, 40 ml of glycol and 10 ml of water. At 80° C., a mixture of 24.7 mg of palladium acetate and 0.55 ml of TPPTS/$H_2O$ solution (0.6 molar) in 2.5 ml of DMSO was added.

After the reaction was complete, the phases were separated. The aqueous phase was washed with 50 ml of toluene. The combined organic phases were washed with 20 ml of water and subsequently dried over sodium sulfate. Crystallization from n-heptane gave 18.7 g of 2-cyano-4'-methylbiphenyl.

Example 17

15 g of 2-chlorobenzonitrile, 14.8 g of p-tolueneboronic acid and 15.8 g of potassium fluoride are heated to 120° C. with 50 ml of p-xylene, 40 ml of diethylene glycol and 10 ml of water. At 80° C., a mixture of 24.7 mg of palladium acetate and 0.55 ml of TPPTS/$H_2O$ solution (0.6 molar) in 2.5 ml of DMSO was added.

After the reaction was complete, the phases were separated. The aqueous phase was washed with 50 ml of toluene. The combined organic phases were wahsed with 20 ml of water and subsequently dried over sodium sulfate. Crystallization from n-heptane gave 17.8 g of 2-cyano-4'-methylbiphenyl.

Example 18

15 g of 2-chlorobenzonitrile, 14.8 g of p-tolueneboronic acid and 15.8 g of potassium fluoride were heated to 120° C. with 50 ml of p-xylene, 40 ml of triethylene glycol and 10 ml of water. At 80° C., a mixture of 24.7 mg of palladium acetate and 0.55 ml of TPPTS/$H_2O$ solution (0.6 molar) in 2.5 ml of DMSO was added.

After the reaction was complete, the phases were separated. The aqueous phase was washed with 50 ml of toluene. The combined organic phases were washed with 20 ml of water and subsequently dried over sodium sulfate. Crystallization from n-heptane gave 17.2 g of 2-cyano-4'-methylbiphenyl.

Example 19

15 g of 2-chlorobenzonitrile, 14.8 g of p-tolueneboronic acid and 15.8 g of potassium fluoride were heated to 120° C. with 50 ml of p-xylene, 40 ml of diethanolamine and 10 ml of water. At 80° C., a mixture of 24.7 mg of palladium acetate and 0.55 ml of TPPTS/$H_2O$ solution (0.6 molar) in 2.5 ml of DMSO was added.

After the reaction was complete, the phases were separated. The aqueous phase was washed with 50 ml of toluene. The combined organic phases were washed with 20 ml of water and subsequently dried over sodium sulfate. Crystallization from n-heptane gave 16.9 g of 2-cyano-4'-methylbiphenyl.

Example 20

15 g of chlorobenzonitrile, 14.8 g of p-tolueneboronic acid and 15.8 g of potassium fluoride were heated to 120° C. with 50 ml of p-xylene, 40 ml of triethanolamine and 10 ml of water. At 80° C., a mixture of 24.7 mg of palladium acetate and 0.55 ml of TPPTS/$H_2O$ solution (0.6 molar) in 2,5 ml of DMSO was added.

After the reaction was complete, the phases were separated. The aqueous phase was washed with 50 ml of toluene. The combined organic phases were washed with 20 ml of water and subsequently dried over sodium sulfate. Crystallization from n-heptane gave 17.2 g of 2-cyano-4'-methylbiphenyl.

Example 21

15 g of 2-chlorobenzonitrile, 14.8 g of p-tolueneboronic acid and 28.9 g of sodium carbonate were heated to 120° C. with 50 ml of p-xylene, 40 ml of glycol and 10 ml of water. At 80° C., a mixture of 38.66 mg of palladium(II) chloride and 1.1 ml of TPPTS/$H_2O$ solution (0.6 molar) in 2.5 ml of DMSO was added.

After the reaction was complete, the phases were separated. The aqueous phase was washed with 50 ml of toluene. The combined organic phases were washed with 20 ml of water and subsequently dried over sodium sulfate. Crystallization from n-heptane gave 18.5 g of 2-cyano-4'-methylbiphenyl.

Example 22

15 g of 2-chlorobenzonitrile, 14.8 g of p-tolueneboronic acid and 28.9 g of sodium carbonate were heated to 120° C. with 50 ml of p-xylene, 40 ml of glycerol and 10 ml of water. At 80° C., a mixture of 38.66 mg of palladium(II) chloride and 1.1 ml of TPPTS/$H_2O$ solution (0.6 molar) in 2.5 ml of DMSO was added.

After the reaction was complete, the phases were separated. The aqueous phase was washed with 50 ml of toluene. The combined organic phases were washed with 20 ml of water and subsequently dried over sodium sulfate. Crystallization from n-heptane gave 18.2 g of 2-cyano-4'-methylbiphenyl.

Example 23

15 g of 2-chlorobenzonitrile, 14.8 g of p-tolueneboronic acid and 28.9 g of sodium carbonate were heated to 120° C. with 50 ml of p-xylene, 40 ml of triethylene glycol and 10 ml of water. At 80° C., a mixture of 38.66 mg of palladium (II) chloride and 1.1 ml of TPPTS/$H_2O$ solution (0.6 molar) in 2.5 ml of DMSO was added.

After the reaction was complete, the phases were separated. The aqueous phase was washed with 50 ml of toluene. The combined organic phases were washed with 20 ml of water and subsequently dried over sodium sulfate. Crystallization from n-heptane gave 17.4 g of 2-cyano-4'-methylbiphenyl.

Example 24

15 g of 2-chlorobenzonitrile, 14.8 g of p-tolueneboronic acid and 28.9 g of sodium carbonate were heated to 120° C. with 50 ml of p-xylene, 40 ml of diethylene glycol and 10 ml of water. At 80° C., a mixture of 38.66 mg of palladium (II) chloride and 1.1 ml of TPPTS/$H_2O$ solution (0.6 molar) in 2.5 ml of DMSO was added.

After the reaction was complete, the phases were separated. The aqueous phase was washed with 50 ml of toluene. The combined organic phases were washed with 20 ml of water and subsequently dried over sodium sulfate. Crystallization from n-heptane gave 17.1 g of 2-Cyano-4'-methylbiphenyl.

Example 25

15 g of 2-chlorobenzonitrile, 14.8 g of p-tolueneboronic acid and 28.9 g of sodium carbonate were heated to 120° C. with 50 ml of p-xylene, 40 ml of diethanolamine and 10 ml of water. At 80° C., a mixture of 38.66 mg of palladium(II) chloride and 1.1 ml of TPPTS/$H_2O$ solution (0.6 molar) in 2.5 ml of DMSO was added.

After the reaction was complete, the phases were separated. The aqueous phase was washed with 50 ml of toluene. The combined organic phases were washed with 20 ml of water and subsequently dried over sodium sulfate. Crystallization from n-heptane gave 17.5 g of 2-cyano-4'-methylbiphenyl.

Example 26

15 g of 2-chlorobenzonitrile, 14.8 g of p-tolueneboronic acid and 28.9 g of sodium carbonate were heated to 120° C.

with 50 ml of p-xylene, 40 ml of triethanolamine and 10 ml of water. At 80° C., a mixture of 38.66 mg of palladium(II) chloride and 1.1 ml of TPPTS/H$_2$O solution (0.6 molar) in 2.5 ml of DMSO was added.

After the reaction was complete, the phases were separated. The aqueous phase was washed with 50 ml of toluene. The combined organic phases were washed with 20 ml of water and subsequently dried over sodium sulfate. Crystallization from n-heptane gave 17.8 g of 2-cyano-4'-methylbiphenyl.

Example 27

15 g of 2-chlorobenzonitrile, 14.8 g of p-tolueneboronic acid and 15.8 g of potassium fluoride were heated to 120° C. with 50 ml of p-xylene, 40 ml of glycerol and 10 ml of water. At 80° C., a mixture of 38.66 mg of palladium(II) chloride and 1.1 ml of TPPTS/H$_2$O solution (0.6 molar) in 2.5 ml of DMSO was added.

After the reaction was complete, the phases were separated. The aqueous phase was washed with 50 ml of toluene. The combined organic phases were washed with 20 ml of water and subsequently dried over sodium sulfate. Crystallization from n-heptane gave 18.9 g of 2-cyano-4'-methylbiphenyl.

Example 28

15 g of 2-chlorobenzonitrile, 14.8 g of p-toluene boronic acid and 15.8 g of potassium fluoride were heated to 120° C. with 50 ml of p-xylene, 40 ml of glycol and 10 ml of water. At 80° C., a mixture of 38.66 mg of palladium(ll) chloride and 1.1 ml of TPPTS/H$_2$O solution (0.6 molar) in 2.5 ml of DMSO was added.

After the reaction was complete, the phases were separated. The aqueous phase was washed with 50 ml of toluene. The combined organic phases were washed with 20 ml of water and subsequently dried over sodium sulfate. Crystallization from n-heptane gave 18.8 g of 2-cyano-4'-methylbiphenyl.

Example 29

15 g of 2-chlorobenzonitrile, 14.8 g of p-tolueneboronic acid and 15.8 g of potassium fluoride were heated to 120° C. with 50 ml of p-xylene, 40 ml of diethylene glycol and 10 ml of water. At 80° C., a mixture of 38.66 mg of palladium (ll) chloride and 1.1 ml of TPPTS/H$_2$O solution (0.6 molar) in 2.5 ml of DMSO was added.

After the reaction was complete, the phases were separated. The aqueous phase was washed with 50 ml of toluene. The combined organic phases were washed with 20 ml of water and subsequently dried over sodium sulfate. Crystallization from n-heptane gave 18.0 g of 2-cyano-4'-methylbiphenyl.

Example 30

15 g of 2-chlorobenzonitrile, 14.8 g of p-tolueneboronic acid and 15.8 g of potassium fluoride were heated to 120° C. with 50 ml of p-xylene, 40 ml of triethylene glycol and 10 ml of water. At 80° C., a mixture of 38.66 mg of palladium (II) chloride and 1.1 ml of TPPTS/H$_2$O solution (0.6 molar) in 2.5 ml of DMSO was added.

After the reaction was complete, the phases were separated. The aqueous phase was washed with 50 ml of toluene. The combined organic phases were washed with 20 ml of water and subsequently dried over sodium sulfate. Crystallization from n-heptane gave 16.9 g of 2-cyano-4'-methylbiphenyl.

Example 31

15 g of 2-chlorobenzonitrile, 14.8 g of p-tolueneboronic acid and 15.8 g of potassum fluoride were heated to 120° C. with 50 ml of p-xylene, 40 ml of diethanolamine and 10 ml of water. At 80° C., a mixture of 38.66 mg of palladium(II) chloride and 1.1 ml of TPPTS/H$_2$O solution (0.6 molar) in 2.5 ml of DMSO was added.

After the reaction was complete, the phases were separated. The aqueous phase was washed with 50 ml of toluene. The combined organic phases were washed with 20 ml of water and subsequently dried over sodium sulfate. Crystallization from n-heptane gave 17.1 g of 2-cyano-4'-methylbiphenyl.

Example 32

15 g of 2-chlorobenzonitrile, 14.8 g of p-tolueneboronic acid and 15.8 g of potassium fluoride were heated to 120° C. with 50 ml of p-xylene, 40 ml of triethanolamine and 10 ml of water. At 80° C., a mixture of 38.66 mg of palladium(II) chloride and 1.1 ml of TPPTS/H$_2$O solution (0.6 molar) in 2.5 ml of DMSO was added.

After the reaction was complete, the phases were separated. The aqueous phase was washed with 50 ml of toluene. The combined organic phases were washed with 20 ml of water and subsequently dried over sodium sulfate. Crystallization from n-heptane gave 18.0 g of 2-cyano-4'-methylbiphenyl.

Example 33

15 g of 2-chlorobenzonitrile, 14.8 g of p-tolueneboronic acid and 28.9 g of sodium carbonate were heated to 120° C. with 50 ml of p-xylene, 40 ml of glycol and 10 ml of water. At 80° C., 19.3 mg of palladium chloride, 17.9 mg of sodium acetate and 0.55 ml of TPPTS/H$_2$O solution (0.6 molar) in 2.5 ml of DMSO were added.

After the reaction was complete, the phases were separated. The aqueous phase was washed with 50 ml of toluene. The combined organic phases were washed with 20 ml of water and subsequently dried over sodium sulfate. Crystallization from n-heptane gave 18.7 g of 2-cyano-4'-methylbiphenyl.

Example 34

15 g of 2-chlorobenzonitrile, 14.8 g of p-tolueneboronic acid and 28.9 g of sodium carbonate were heated to 120° C. with 50 ml p-xylene, 40 ml of glycerol and 10 ml of water. At 80° C., a mixture of 19.3 mg of palladium chloride, 17.9 mg sodium acetate and 0.55 ml of TPPTS/H$_2$O solution (0.6 molar) in 2.5 ml of DMSO was added.

After the reaction was complete, the phases were separated. The aqueous phase was washed with 50 ml of toluene. The combined organic phases were washed with 20 ml of water and subsequently dried over sodium sulfate. Crystallization from n-heptane gave 18.3 g of 2-cyano-4'- methylbiphenyl.

Example 35

15 g of 2-chlorobenzonitrile, 14.8 g of p-tolueneboronic acid and 28.9 g of sodium carbonate were heated to 120° C. with 50 ml of p-xylene, 40 ml of triethylene glycol and 10 ml of water. At 80° C., a mixture of 19.3 mg of palladium chloride, 17.9 mg of sodium acetate and 0.55 ml of TPPTS/ H₂O solution (0.6 molar) in 2.5 ml of DMSO was added.

After the reaction was complete, the phases were separated. The aqueous phase was washed with 50 ml of toluene. The combined organic phases were washed with 20 ml of water and subsequently dried over sodium sulfate. Crystallization from n-heptane gave 17.4 g of 2-cyano-4'-methylbiphenyl.

Example 36

15 g of 2-chlorobenzonitrile, 14.8 g of p-tolueneboronic acid and 28.9 g of sodium carbonate were heated to 120° C. with 50 ml of p-xylene, 40 ml of diethylene glycol and 10 ml of water. At 80° C., a mixture of 19.3 mg of palladium chloride, 17.9 mg of sodium acetate and 0.55 ml of TPPTS/ H₂O solution (0.6 molar) in 2.5 ml of DMSO was added.

After the reaction was complete, the phases were separated. The aqueous phase was washed with 50 ml of toluene. The combined organic phases were washed with 20 ml of water and subsequently dried over sodium sulfate. Crystallization from n-heptane gave 18.3 g of 2-cyano-4'-methylbiphenyl.

Example 37

15 g of 2-chlorobenzonitrile, 14.8 g of p-tolueneboronic acid and 28.9 g of sodium carbonate were heated to 120° C. with 50 ml of p-xylene, 40 ml of diethanolamine and 10 ml of water. At 80° C., a mixture of 19.3 mg of palladium chloride, 17.9 mg of sodium acetate and 0.55 ml of TPPTS/ H₂O solution (0.6 molar) in 2.5 ml of DMSO was added. After the reaction was complete, the phases were separated. The aqueous phase was washed with 50 ml of toluene. The combined organic phases were washed with 20 ml of water and subsequently dried over sodium sulfate. Crystallization from n-heptane gave 17.5 g of 2-cyano-4'-methylbiphenyl.

Example 38

15 g of 2-chlorobenzonitrile, 14.8 g of p-tolueneboronic acid and 28.9 g of sodium carbonate were heated to 120° C. with 50 ml of p-xylene, 40 ml of triethanolamine and 10 ml of water. At 80° C., 19.3 mg of palladium chloride, 17.9 mg of sodium acetate and 0.55 ml of TPPTS/H₂O solution (0.6 molar) in 2.5 ml of DMSO were added.

After the reaction was complete, the phases were separated. The aqueous phase was washed with 50 ml of toluene. The combined organic phases were washed with 20 ml of water and subsequently dried over sodium sulfate. Crystallization from n-heptane gave 17.8 g of 2-cyano-4'-methylbiphenyl.

Example 39

15 g of 2-chlorobenzonitrile, 14.8 g of p-tolueneboronic acid and 28.9 g of sodium carbonate were heated to 120° C. with 50 ml of p-xylene, 40 ml of DMSO and 10 ml of water. At 80° C., a mixture of 24.7 mg of palladium acetate(II) and 0.55 ml of TPPTS/H₂O (0.6 molar) in 2.5 ml of DMSO was added.

After the reaction was complete, the phases were separated. The aqueous phase was washed with 50 ml of xylene. The combined organic phases were washed with 20 ml of water and subsequently dried over sodium sulfate. The solvent was evaporated and the residue was crystallized from n-heptane. Yield: 18.6 g (88% of theory) of 2-cyano-4'-methylbiphenyl.

Example 40

15 g of 2-chlorobenzonitrile, 14.8 g of p-tolueneboronic acid and 29.8 g of sodium carbonate were heated to 120° C. with 50 ml of p-xylene, 40 ml of sulfolane and 10 ml of water. At 80° C., a mixture of 24.7 mg of palladium acetate and 0.55 ml of TPPTS/H₂O solution (0.6 molar) in 2.5 ml of DMSO was added.

After the reaction was complete, the phases were separated. The aqueous phase was washed with 50 ml of xylene. The combined organic phases were washed with 20 ml of water and subsequently dried over sodium sulfate. The solvent was evaporated and the residue was crystallized from n-heptane. Yield: 19.2 g (91% of theory) of 2-cyano-4'-methylbiphenyl.

Example 41

15 g of 2-chlorobenzonitrile, 14.8 g of p-tolueneboronic acid and 28.9 g of sodium carbonate were heated to 120° C. with 50 ml of p-xylene, 40 ml of DMSO and 10 ml of water. At 80° C., a mixture of 38.66 mg of palladium(II) chloride and 1.1 ml of TPPTS/H₂O solution (0.6 molar) in 2.5 ml of DMSO was added.

After the reaction was complete, the phases were separated. The aqueous phase was washed with 50 ml of xylene. The combined organic phases were washed with 20 ml of water and subsequently dried over sodium sulfate. The solvent was evaporated and the residue was crystallized from n-heptane. Yield: 18.2 g (86% of theory) of 2-cyano-4'-methylbiphenyl.

Example 42

15 g of 2-chlorobenzonitrile, 14.8 g of p-tolueneboronic acid and 28.9 g of sodium carbonate were heated to 120° C. with 50 ml of p-xylene, 40 ml of sulfolane and 10 ml of water. At 80° C., a mixture of 38.66 mg of palladium(II) chloride and 1.1 ml of TPPTS/H₂O solution (0.6 molar) in 2.5 ml of DMSO was added.

After the reaction was complete, the phases were separated. The aqueous phase was washed with 50 ml of xylene. The combined organic phases were washed with 20 ml of water and subsequently dried over sodium sulfate. The solvent was evaporated and the residue was crystallized from n-heptane. Yield: 18.4 g (87% of theory) of 2-cyano-4'-methylbiphenyl.

Example 43

15 g of 2-chlorobenzonitrile, 14.8 g of p-tolueneboronic acid and 28.9 g of sodium carbonate were heated to 120° C. with 50 ml of p-xylene, 40 ml of DMSO and 10 ml of water. At 80° C., a mixture of 19.3 mg of palladium(II) chloride, 17.9 mg of sodium acetate and 0.55 ml of TPPTS/H₂O solution (0.6 molar) in 2.5 ml of DMSO was added.

After the reaction was complete, the phases were separated. The aqueous phase was washed with 50 ml of xylene. The combined organic phases were washed with 20 ml of water and subsequently dried over sodium sulfate. The solvent was evaporated and the residue was crystallized from n-heptane. Yield: 18.8 g (89% of theory) of 2-cyano-4'-methylbiphenyl.

Example 44

15 g of 2-chlorobenzonitrile, 14.8 g of p-tolueneboronic acid and 28.9 9 of sodium carbonate were heated to 120° C. with 50 ml of p-xylene, 40 ml of sulfolane and 10 ml of water. At 80° C., a mixture of 19.3 mg of palladium(II) chloride, 17.9 mg of sodium acetate and 0.55 ml of TPPTS/ H₂O solution (0.6 molar) in 2.5 ml of DMSO was added.

After the reaction was complete, the phases were separated. The aqueous phase was washed with 50 ml of xylene.

The combined organic phases were washed with 20 ml of water and subsequently dried over sodium sulfate. The solvent was evaporated and the residue was crystallized from n-heptane. Yield: 18.9 g (89.5% of theory) of 2-cyano-4'-methylbiphenyl.

Example 45

15 g of 2-chlorobenzonitrile, 14.8 g of p-tolueneboronic acid and 28.9 g of sodium carbonate were heated to 120° C. with 50 ml of p-xylene and 40 ml of DMSO. At 80° C., a mixture of 24.7 mg of palladium acetate (II) and 0.55 ml of TPPTS/$H_2O$ solution (0.6 molar) in 2.5 ml of DMSO was added.

After the reaction was complete, the phases were separated. The aqueous phase was washed with 50 ml of xylene. The combined organic phases were washed with 20 ml of water and subsequently dried over sodium sulfate. The solvent was evaporated and the residue was crystallized from n-heptane. Yield: 18.0 g (85% of theory) of 2-cyano-4'-methylbiphenyl.

Example 46

15 g of 2-chlorobenzonitrile, 14.8 g of p-tolueneboronic acid and 28.9 g of sodium carbonate were heated to 120° C. with 50 ml of p-xylene and 40 ml of sulfolane. At 80° C., a mixture of 24.7 mg of palladium acetate(II) and 0.55 ml of TPPTS/$H_2O$ solution (0.6 molar) in 2.5 ml of DMSO was added.

After the reaction was complete, the phases were separated. The aqueous phase was washed with 50 ml of xylene. The combined organic phases were washed with 20 ml of water and subsequently dried over sodium sulfate. The solvent was evaporated and the residue was crystallized from n-heptane. Yield: 18.2 g (86% of theory) of 2-cyano-4'-methylbiphenyl.

Comparative Example 15 g of 2-chlorobenzonitrile, 14.8 g of p-tolueneboronic acid and 28.9 g of sodium carbonate were heated to 120° C. with 50 ml of p-xylene and 40 ml of DMF. At 80° C., a mixture of 24.7 mg of palladium acetate (II) and 0.55 ml of TPPTS/$H_2O$ solution (0.6 molar) in 2.5 ml of DMF was added.

After the reaction was complete, the phases were separated. The aqueous phase was washed with 50 ml of xylene. The combined organic phases were washed with 20 ml of water and subsequently dried over sodium sulfate. The solvent was evaporated and the residue was crystallized from n-heptane. Yield: 1.06 g (5% of theory) of 2-cyano-4'-methylbiphenyl.

Example 47
Cross-coupling of 2-chlorobenzonitrile with 4-tolueneboronic acid To prepare the catalyst, 38.8 mg (0.219 mmol) of palladium(II) chloride and 54.0 mg (0.657 mmol) of sodium acetate are stirred for 30 minutes at 23° C. in 2.4 ml of DMSO under an argon atmosphere. Subsequently, 1.99 ml (0.875 mmol) of a 0.44 molar aqueous solution of sodium 4-diphenylphosphinophenylphosphinate, prepared as described below, are added and the suspension is stirred for a further 30 minutes at 23° C. Under an argon atmosphere, 30.0 g (0.2181 mol) of 2-chlorobenzonitrile, 32.6 g (0.240 mol) of 4-tolueneboronic acid and 16.2 g (70 mol %) of sodium carbonate are stirred into 120 ml of ethylene glycol.

20 ml of water are added and the mixture is heated to 80° C. The above-described catalyst suspension is then added and the mixture is heated for 5 hours under reflux.

At 23° C., the mixture is admixed with 100 ml of ethyl acetate. The organic phase is separated off, evaporated on a rotary evaporator and fractionally distilled under reduced pressure. This gives 31.6 g (75% of theory) of 2-cyano-4'-methylbiphenyl (bp. 140° C./1.0 mbar; mp. 50° C.).
Preparation of the catalyst:
a) Isobutyl 4-fluorophenylmethylphosphinate A mixture of 50.0 g (289 mmol) of 4-bromofluorobenzene, 43.3 g (318 mmol) of isobutyl methanephosphonite, 43.8 ml (318 mmol) of triethylamine, 1.64 g (0.29 mmol, 1 mol %) of bis(dibenzylideneacetone)-palladium and 1.50 g (0.58 mmol, 2 mol %) of triphenylphosphine was heated for 20 hours at 100° C. under an inert gas atmosphere. At 23° C., the solution was filtered off from the ammonium salt formed and the filtrate was evaporated under reduced pressure. Fractional distillation under reduced pressure gave 54.60 g (83% of theory) of isobutyl 4-fluorophenylmethylphosphinate having a boiling point of 83° C./0.08 mbar.

b) Isobutyl (4-diphenylphosphinophenyl)methylphosphinate 200 ml (100 mmol) of potassium diphenylphosphide solution in THF (manufacturer: Aldrich) were added dropwise at −5° C. to a solution of 21.90 g (95 mmol) of isobutyl 4-fluorophenylmethylphosphinate in 150 ml of THF. After stirring for 20 hours at 23° C., the mixture was hydrolyzed by addition of 250 ml of degassed water and stirring for 15 minutes. Extraction with ethyl acetate, drying of the organic phase over $Na_2SO_4$, evaporation on a rotary evaporator and drying under reduced pressure gave 37.0 g of isobutyl (4-diphenylphosphinophenyl)methylphosphinate in the form of a yellow oil.

c) (4-Diphenylphosphinophenyl)methylphosphinic acid 8.70 g (2127.5 mmol) of NaOH in 40 ml of water were added dropwise at 23° C. to a solution of 34.52 g (87 mmol) of isobutyl (4-diphenylphosphino-phenyl)methylphosphinate in 50 ml of THF. After heating under reflux for 6 hours, 18.1 ml (218 mmol) of concentrated hydrochloric acid were added dropwise at 23° C., the mixture was stirred for 10 minutes at 23° C. and completely evaporated on a rotary evaporator. The residue is taken up in methylene chloride, the solution was dried over $Na_2SO_4$ and completely evaporated. Drying under reduced pressure gave 28.3 g of (4-diphenylphosphinophenyl)methylphosphinic acid (90% of theory) in the form of a pale yellow solid having a melting point of 40° C.

d) Sodium (4-diphenylphosphinophenyl)methylphosphinate
15.0 g (44.1 mmol) of (4-diphenylphosphinophenyl)methylphosphinic acid were admixed with 100 ml of a 3.7% strength by weight sodium hydrogen carbonate solution (44.1 mmol of $NaHCO_3$) and stirred at room temperature until $CO_2$ evolution had ceased. The aqueous solution was completely evaporated and dried under reduced presure. This gave 15.6 g (97% of theory) of sodium (4-diphenylphosphinophenyl)methyl-phosphinate. Solubility in water: 590 g/l.

What is claimed is:
1. A process for preparing polycyclic aromatic compounds, which comprises reacting
   a) an aromatic boron compound with
   b) an aromatic halogen compound or an aromatic perfluoroalkylsulfonate in the presence of
   c) a base selected from the group consisting of alkali metal and alkaline earth metal hydroxides alkali metal and alkaline earth metal carbonates, alkali metal hydrogen carbonates, alkali metal and alkaline earth metal acetates, alkali metal and alkaline earth metal alkoxides, and also primary, secondary and tertiary amines, d) nickel or palladium catalyst solution, e) a phosphorous-containing ligand and f) a polyhydric alcohol, a sulfoxide or sulfone.

2. The process as claimed in claim 1, wherein the polyhydric alcohol, the sulfoxide or sulfone are water-soluble.

3. The process as claimed in claim 1, wherein the polyhydric water-soluble alcohol is selected from the group consisting of glycols, glycerol, oligoglycerides which can also be partially esterified, diethylene, triethylene and tetraethylene glycols or polyethylene glycols of the formula (I),

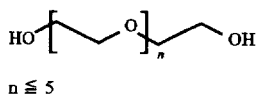 (I)

$n \leq 5$ polyhydric alkanols or alkenols, polyhydric cycloalkanols, polyhydric, aryl-containing alkanols, polyhydric aminoalcohols, polyhydric iminoalcohols.

4. The process as claimed in claim 1, wherein use is made of a sulfoxide or sulfone of the formula (II),

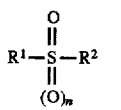 (II)

n = 0, sulfoxide
n = 1, sulfone where $R^1$, $R^2$ are aliphatic or aromatic hydrocarbons which may be unsubstituted, substituted or linked to one another.

5. The process as claimed in claim 1, wherein the phosphorus-containing ligand is selected from the group consisting of tri-n-alkylphosphines, triarylphosphines, dialkylarylphosphines, alkyldiarylphosphines and heteroarylphosphines, where the three substituents on the phosphorus can be identical or different, chiral or achiral and where one or more of the substituents can link the phosphorus groups of a plurality of phosphines and where part of this linkage can also be one or more metal atoms, phosphites, phosphinous esters and phosphonous esters, phosphols, dibenzophosphols and phosphorus-containing cyclic, oligocyclic or polycyclic compounds.

6. The process as claimed in claim 5, wherein the phosphorus-containing ligand is water-soluble.

7. The process as claimed in claim 1, wherein the aromatic boron compound has the formula (II),

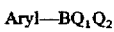 (II)

where

Aryl is an aromatic radical and $Q_1$, $Q_2$ are identical or different and are —OH, $C_1$–$C_4$-alkoxy, $C_1$–$C_4$-alkyl, phenyl which may be unsubstituted or substituted by $C_1$–$C_4$-alkyl, $C_1$–$C_4$-alkoxy or halogen, or halogen or $Q_1$ and $Q_2$ together form a $C_1$–$C_4$-alkylenedioxy group, or $Q_1$ and $Q_2$ and the boron atom are together part of a boroxane ring of the formula (III):

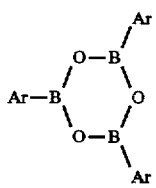 (III)

8. The process as claimed in claim 1, wherein use is made of an aromatic chlorine compound.

9. The process as claimed in claim 1, wherein the aromatic boron compound is p-tolueneboronic acid and the aromatic halogen compound is chlorobenzonitrile.

* * * * *